United States Patent [19]

Cormier et al.

[11] 4,399,362
[45] Aug. 16, 1983

[54] LIQUID HANDLING APPARATUS

[75] Inventors: Alan D. Cormier, Newburyport; John D. Czaban, Bradford; Thomas J. Schillinger, Stoughton; Kenneth D. Legg, Wellesley; Thomas F. Kelley, Canton, all of Mass.

[73] Assignee: Instrumentation Laboratory Inc., Lexington, Mass.

[21] Appl. No.: 239,025

[22] Filed: Feb. 27, 1981

[51] Int. Cl.³ ............................................. G01N 21/01
[52] U.S. Cl. .................................... 250/430; 250/435; 250/432 R; 422/82
[58] Field of Search ........................ 250/430, 432, 435; 422/82

[56] References Cited

U.S. PATENT DOCUMENTS 3,759,667 9/1973 Bannister et al. ...................... 422/82
3,929,413 12/1975 Young et al. .......................... 422/82
4,130,394 12/1978 Negersmith ............................ 422/82
4,253,846 3/1981 Smythe et al. ........................ 422/82

Primary Examiner—Bruce C. Anderson

[57] ABSTRACT

A clinical analyzer system flows a small volume (less than 200 microliters) of liquid sample to be analyzed from an inlet port past a sensor array to a series of analysis chambers. The sensor array includes two optical sensor units that are spaced a fixed distance apart, and each sensor unit transmits a beam of infrared radiation through the flow tube for sensing by a detector. Each detector output has a low value when blood is in the flow tube, an intermediate value when air is in the flow tube, and a high value when a clear liquid is in the flow tube. Control logic senses changes in the outputs of the detectors and accurately indicates gas-liquid interface transitions. The noninvasive system accurately locates leading and trailing edges of samples of biological fluids to be analyzed, monitors the integrity of those samples, and distinguishes between types of sample liquids processed by the analyzer.

8 Claims, 11 Drawing Figures

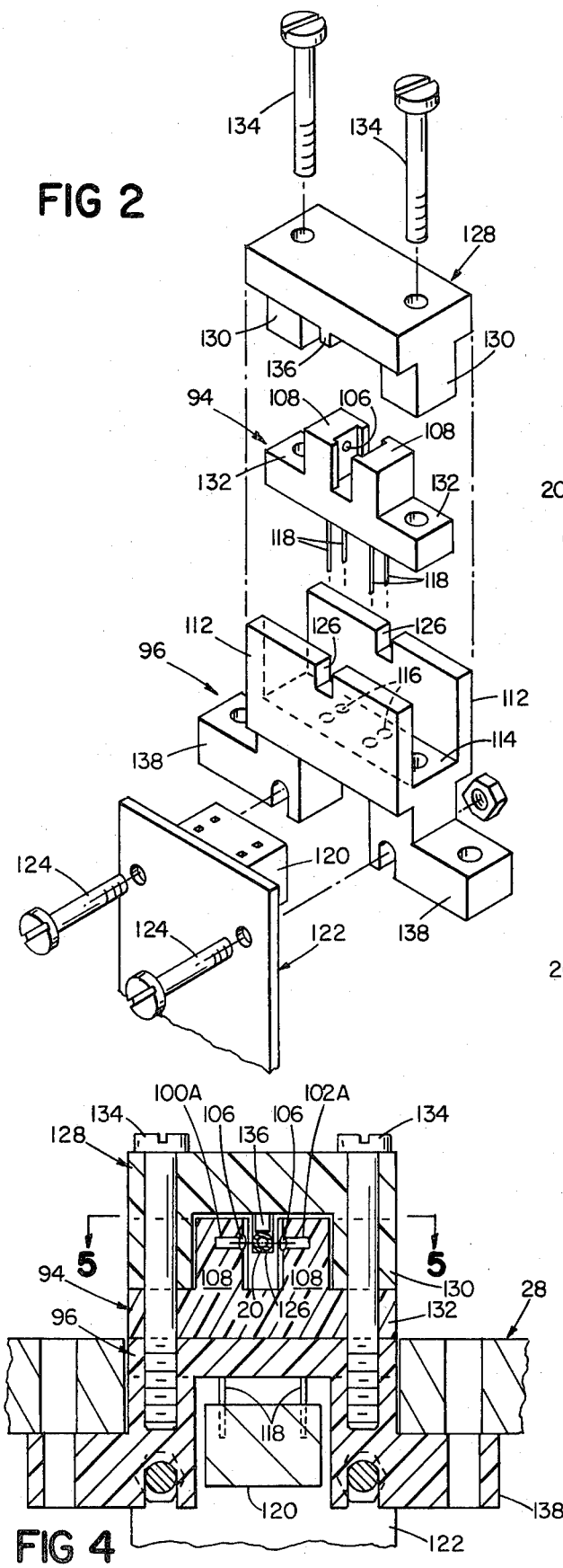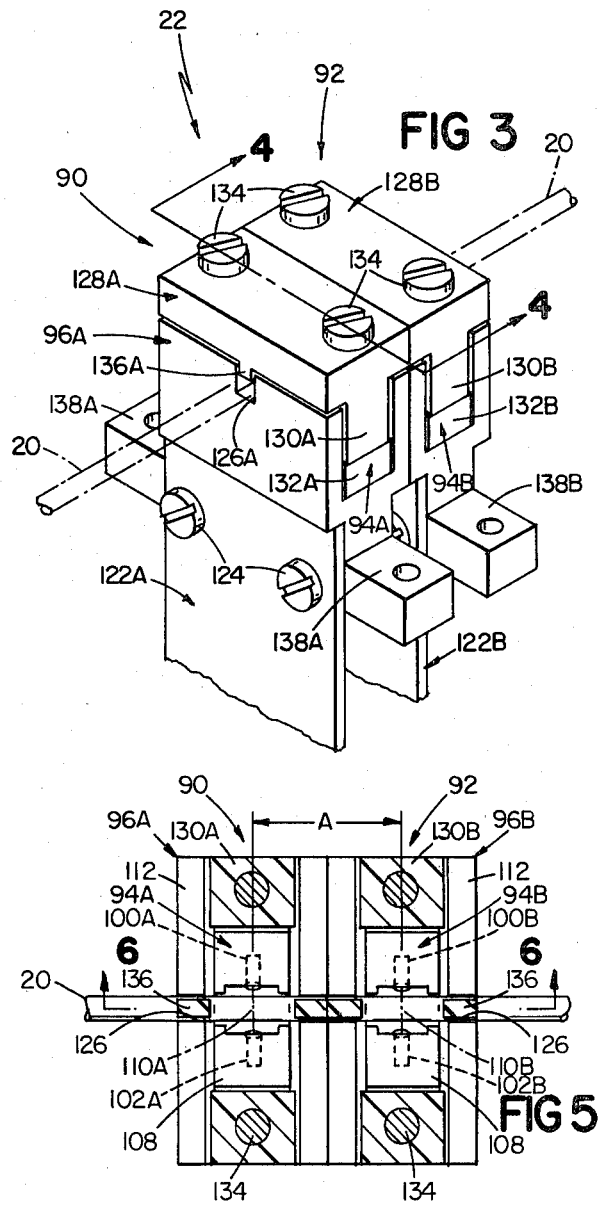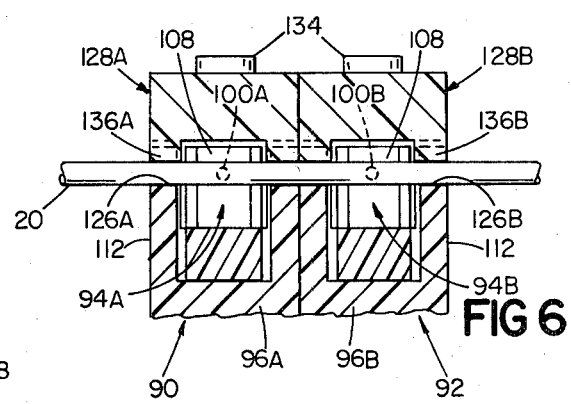

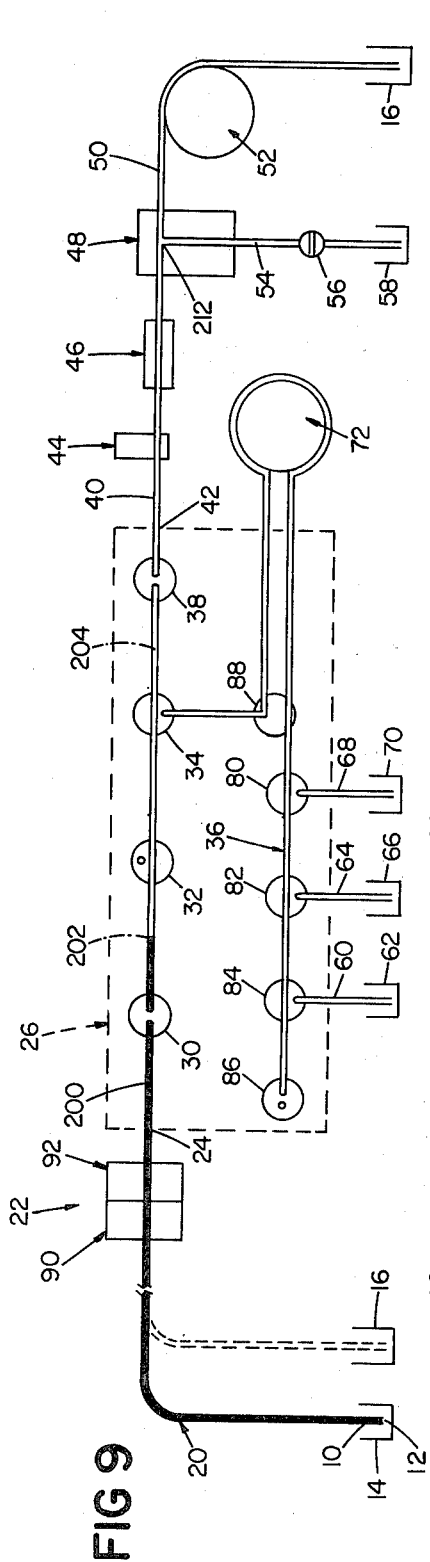
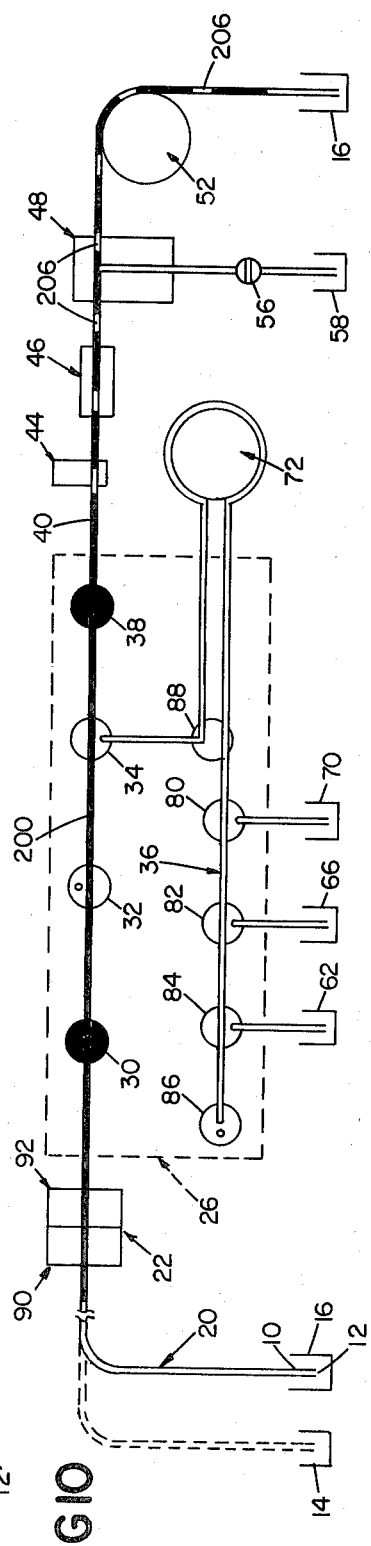
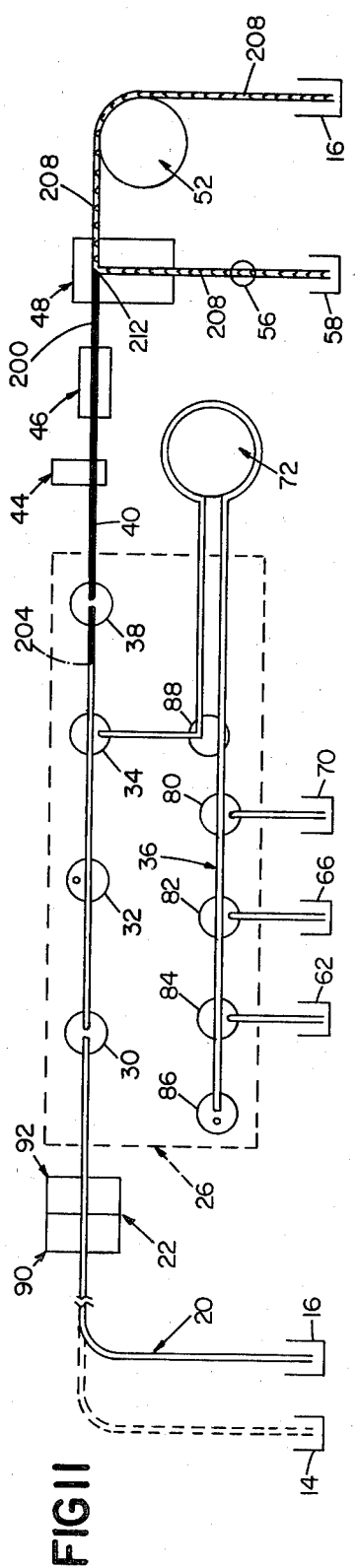

LIQUID HANDLING APPARATUS

This invention relates to liquid handling apparatus and has particular application to systems for handling blood and other biological fluids.

Accurate measurement of one or more constituents of a sample of a biological fluid (whole blood, plasma, urine, etc.) provides useful information for diagnosis, assistance in the control of life support devices, and evaluation of the effectiveness of therapeutic measures. Often, only a limited quantity of the biological fluid is available for analysis, and a minute quantity must be located with precision and integrity (e.g., an absence of air bubbles) relative to one or more analysis regions for exposure to constituent sensors that provide outputs related to the constituents of interest in the liquid sample being analyzed. Such systems frequently analyze a number of different biological fluids and also handle other fluids such as calibrants and flush solutions, and care must be taken to avoid cross-contamination or other interaction between successive fluids, as residue may have adverse effect on the accuracy of measurements. Heretofore, sensors of the electrical conductivity type have been used to sense the presence of liquid in the flow path. Such sensor arrangements have a number of drawbacks, including the difficulty of locating sensor electrodes in the sample flow path, changes in sensor conductivity due to the buildup of protein coatings, the inability of such sensors to distinguish between different liquids (e.g., blood and calibration liquids), the creation of discontinuities in the flow path which may introduce sample contamination, and requirements for careful design to avoid electrical ground problems.

In accordance with one aspect of the invention, there is provided a liquid handling system for controlling the quantity and position of liquids, such as samples of blood to be analyzed, in a flow path. A gas-liquid interface sensor is coupled to the flow path defining structure, and means responsive to the interface sensor operates flow control means to locate liquid at a predetermined position in the flow path.

Preferably, the interface sensor includes a pair of detector units spaced a fixed distance apart along the flow path; and the sensor responsive means responds to the successive sensing of a gas-liquid interface by the two detectors to store a transit time indication of flow velocity of the liquid in the flow path. A detector unit may continue to monitor the liquid in the flow path after detection of a gas-liquid interface, for example, to sense the presence of gas bubbles in the liquid stream, or to distinguish between different types of liquids in the flow path. The transit time (flow velocity) information is used to accurately position leading and trailing edges of a liquid quantity at desired locations in the flow path.

In accordance with another aspect of the invention, there is provided a system for distinguishing between blood and other fluids, including air, in an analysis system or the like that includes a chamber portion for receiving a liquid, the chamber portion having a light transmitting section; and a sensor system that includes a radiation source for transmitting a beam of radiation through the chamber portion at the radiation transmitting section, a detector on the opposite side of the radiation transmitting section for responding to the transmitted beam of radiation, and logic responsive to the output of the detector to provide an indication of the type of fluid in the chamber. The system provides reliable differentiation between blood, air, and other liquids to be processed such as serum, urine, or calibration liquids. The detector output has a median value when air is in the monitored region, a lower value when blood is in the monitored region, and a higher value when a "clear" liquid (that may be intensely colored or may have the same color as blood) is in the monitored region. While the phenomenon is not clearly understood, a "clear" liquid in the monitored region significantly increases radiation transmission characteristics over those present when air in the monitored region.

In a particular embodiment, liquid handling apparatus in accordance with the invention is incorporated in a clinical analyzer system that employs ion selective electrodes for measurement of concentration of sodium and potassium ions. A flow tube extends from an inlet port through a velocity sensor array and a valve array to a series of analysis chambers. In each analysis chamber there is a constituent sensor (e.g., an ion selective membrane of glass or plastic material), and the magnitude of the electrical potential developed at the membrane-sample interface is related to the ionic concentration of the constituent of interest in the sample liquid being analyzed. A peristaltic pump flows a small volume of liquid sample to be analyzed (less than 200 microliters in volume) from the inlet port through the analysis chambers. The sensor array includes two optical sensor units that are spaced a predetermined distance apart along the flow tube, and each sensor unit transmits a beam of infrared radiation through the flow tube for sensing by a detector on the opposite side of the flow tube. The magnitude of the detector output is a function of the fluid in the flow tube, the detector output having a low value when blood is in the flow tube, an intermediate value when air is in the flow tube, and a high value when a clear liquid is in the flow tube. Threshold logic senses changes in the outputs of the detectors and accurately indicate gas-liquid interface transitions (e.g., leading and trailing edges of liquid samples). Control logic responsive to the sensor array stores a transit time pulse count which provides information on the flow velocity of the detected gas-liquid interface. Flow velocities of liquids through the system vary as a function of factors such as the viscosity of the liquid, the pump speed, and the presence of gas segments in the liquid stream (for example, introduction of gas segments into a sample liquid stream creates a trailing edge flow velocity different from the leading edge flow velocity of a liquid sample). The liquid propulsion means in a particular embodiment is a peristaltic pump driven by a stepping motor, and a pump stepping pulse rate is selected as a function of the detected type of liquid. That embodiment also has a backflush mode in which the sensor array is also used to signal depletion of flush liquid.

The invention provides a noninvasive system for accurately locating leading and trailing edges of samples of biological fluids to be analyzed, for monitoring the integrity of those sample, and for distinguishing between types of liquids processed by the analyzer.

Other features and advantages of the invention will be seen as the following description of a particular embodiment progresses, in conjunction with the drawings, in which:

FIG. 2 is a perspective exploded view of components of the velocity sensor employed in the system shown in FIG. 1;

FIG. 3 is a perspective view of the velocity sensor assembly employed in the system shown in FIG. 1;

FIG. 4 is a sectional view taken along the line 4—4 of FIG. 3;

FIG. 5 is a sectional view taken along the line 5—5 of FIG. 4;

FIG. 6 is a sectional view taken along the line 6—6 of FIG. 5;

FIGS. 9-11 are a series of diagrams showing a sequence of positioning a liquid sample in the analyzer shown in FIG. 1.

DESCRIPTION OF PARTICULAR EMBODIMENT

Figure 1:
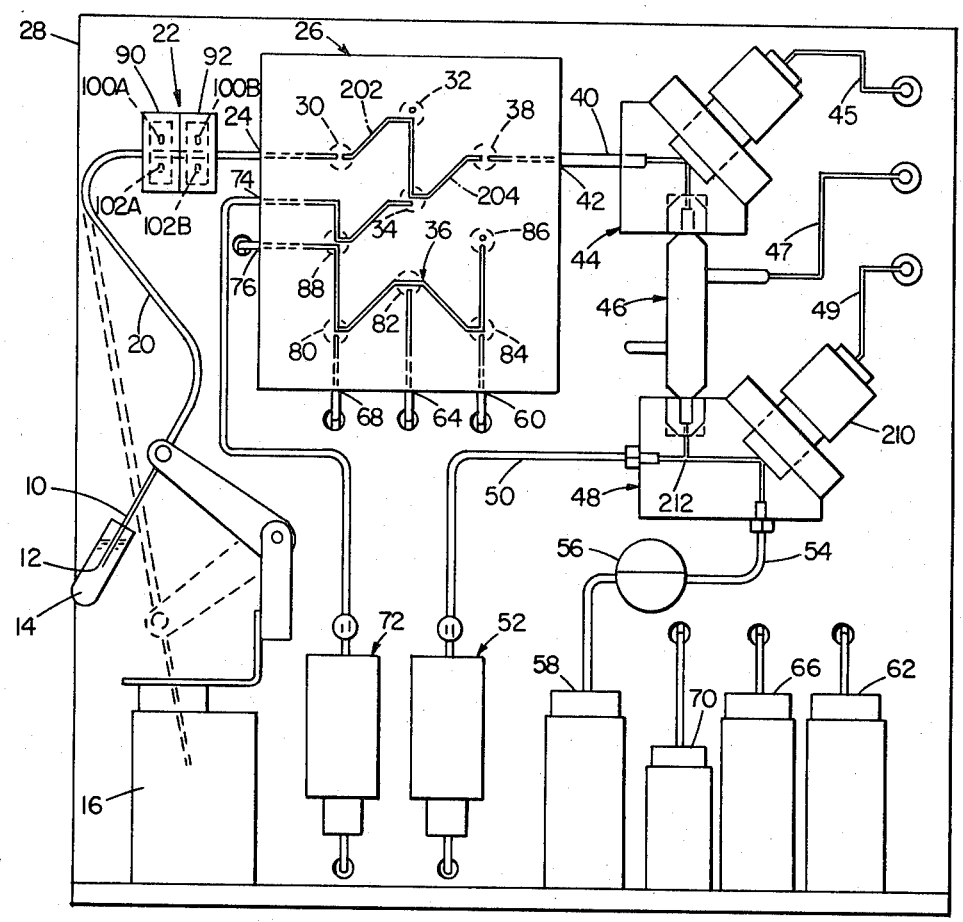
FIG. 1 is a front view of a clinical analyzer instrument in accordance with the invention.

The analysis instrument shown in FIG. 1 includes sample probe 10 that is movable between an extended position in which tip 12 of probe 10 may be inserted in a sample container 14 for withdrawing a sample to be analyzed, and a retracted position in which tip 12 of probe 10 is housed in waste receptacle 16. Flexible conduit 20 extends from sample probe 10 through a sensor array 22 to port 24 of valve array 26. The sample flow path through valve array 26 passes through probe isolation valve 30, vent valve 32, T-valve 34 for connection to manifold 36, and electrode isolation valve 38. Conduit 40 connects output port 42 of valve array 26 to an electrochemical electrode sensor array which includes serial flow through a potassium sensing module 44 that provides an output over line 45, a sodium sensing module 46 that provides an output over line 47, and a reference junction module 48 that provides an output over line 49. Conduit 50 extends from module 48 to waste receptacle 16 via peristaltic pump 52.

Connected to reference junction module 48 through line 54 and pinch valve 56 is a source of reference electrolyte 58. Calibration manifold 36 has a connection through port 60 to a first source 62 of calibration fluid; through port 64 to a second source 66 of calibration fluid; and through port 68 to a source 70 of conditioning fluid for sodium electrode 46. Manifold 36 is also connected to peristaltic pump 72 via ports 74 and 76. Also connected to calibration manifold 36 are three control valves 80, 82, and 84, a vent valve 86, and a bypass valve 88. Further details of valve array 26 and the electrode modules may be had with reference to copending application Ser. No. 165,051 filed July 1, 1980, U.S. Pat. No. 4,283,262 and assigned to the same assignee as this application, which application is expressly incorporated herein by reference.

Tube 20, of 80 Shore A durometer polyurethane, has an outer diameter of about 1.8 millimeter and an inner diameter of about 0.7 millimeter, and extends through sensor array 22, further details of which may be had with reference to FIGS. 2-6. Sensor array 22 includes two sensor units 90, 92 each of which includes an optical switch 94 (Spectronics Inc. Model SPX-1873-1 Optical Switch), disposed in a holder structure 96. Each switch 94 includes an infrared light emitting diode source 100 and an opposed phototransistor sensor 102 and each is hermetically sealed with lens 106 in a pedestal 108 so that the beam 110 of infrared radiation from source 100 is sensed by sensor 102. Each holder structure 96 has upstanding spaced parallel side walls 112 and a base 114 with openings 116 for leads 118 of the switch unit 94. Each switch unit 94 is seated on its corresponding base 114 with leads 118 passing through apertures 116 for connection to pluggable connector unit 120 that is mounted on printed circuit board 122 and secured to holder 96 by fasteners 124. Formed in each side wall 112 of holder 96 is a recess 126 that has a width of about 1.8 millimeter and a depth of about three millimeters and that receives flow tube 20. Holder cover 128 has depending legs 130 that seat on the upper surfaces of flanges 132 of each sensor unit 90, 92, and fasteners 134 extend through cover 128 and flanges 132 to secure each sensor unit in place in its holder. Each cover has two depending projections 136 which enter corresponding holder wall recesses 126.

The two holder assemblies are fixed in side-by-side position as indicated in FIGS. 3, 5, and 6 with holder support projections 138 bolted to the rear surface of the face plate 28 of the analyzer housing. In this position, optical beams 110A and 110B are parallel and spaced about 12 millimeters apart (dimension A indicated in FIG. 5). Flow tube 20 is disposed in aligned support recesses 126 so that it is centered in the optical beams 110A, B; and held in place by cover posts 136, as indicated in FIGS. 4 and 6.

Figure 7:
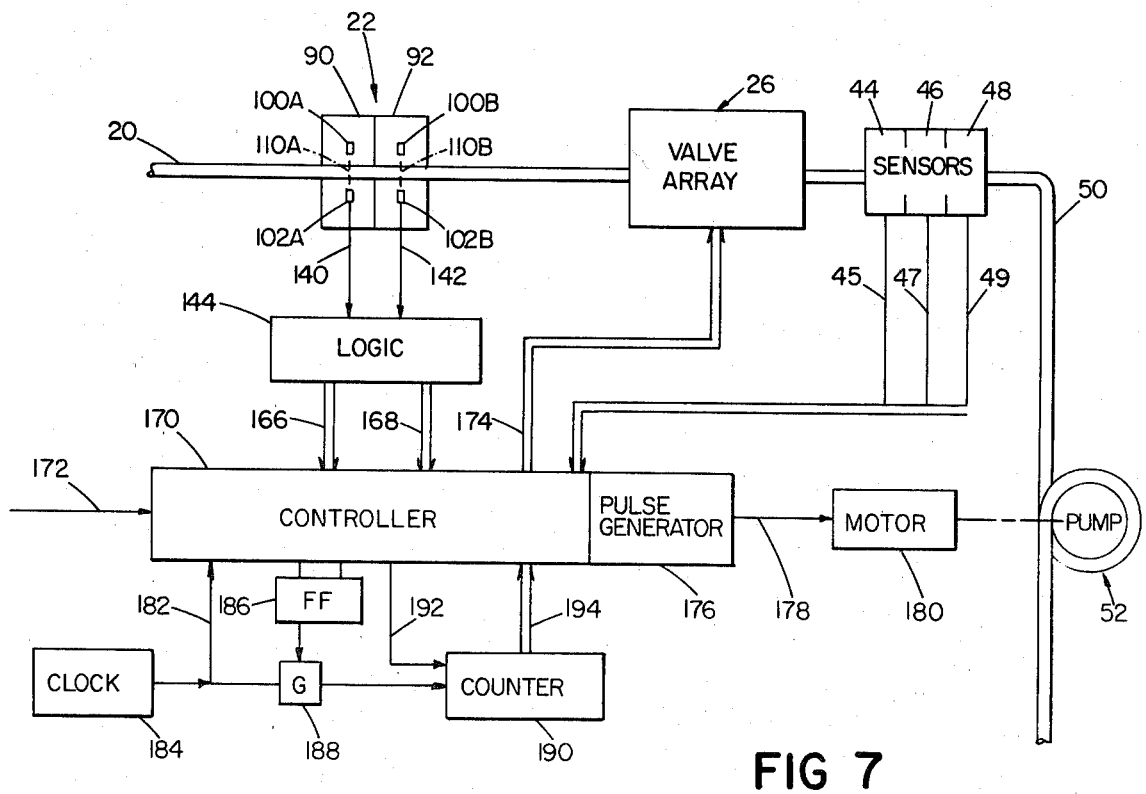
FIG. 7 is a block diagram of the control system employed in the analyzer instrument shown in FIG. 1.
Figure 8:
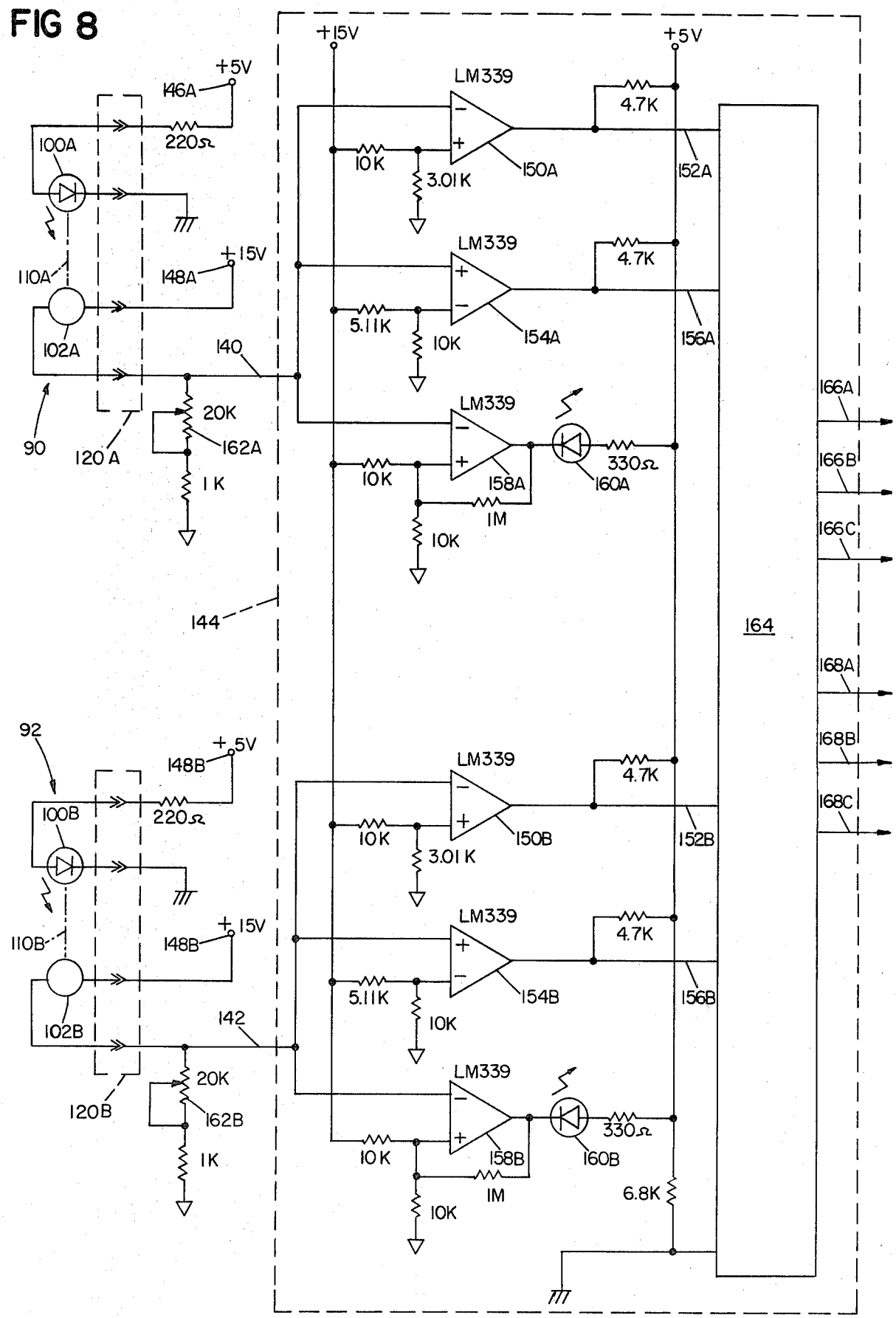
FIG. 8 is a schematic diagram of sensor logic incorporated in the control system of FIG. 7.

Outputs from sensor units 90 and 92 are applied over lines 140, 142 respectively as indicated in FIG. 7, to logic circuit 144, further details of which may be had with reference to FIG. 8. Each LED 100 is connected through pluggable connector 120 to a +5 volt source 146 and to ground; and each phototransistor 102 is connected through pluggable connector 120 to a +15 volt source 148 and to its lines 140, 142 respectively that is connected to logic 144. That logic includes a first threshold (comparator logic) circuit 150 that produces an output on line 152 if the signal on its input line 140 (142) is less than three volts; a second threshold (comparator logic) circuit 154 that produces an output on line 156 if the signal on input line 140 (142) exceeds ten volts; and a reference amplifier circuit 158 that has a light emitting diode 160 in its output circuit. Connected to each input line 140, 142 is a potentiometer 162 that permits adjustment of the voltage on line 140, 142 respectively. Each potentiometer is adjusted so that reference amplifier circuit 158 causes its photodiode 160 to just turn on when there is air in line 20 (an output on line 140 (142) of about 7½ volts).

Thus, with air in tube 20 the voltage on each line 140, 142 is about 7½ volts. With blood in tube 20, radiation transmission is reduced and the voltage on output line 140 (142) drops to about 0.5-1 volt such that threshold logic circuit 150 produces an output on line 152 which indicates the presence of blood in tube 20. With another liquid (e.g., plasma, calibrant or water) in tube 20, radiation transmission increases and the output voltage on line 140 (142) rises to about twelve volts so that threshold circuit 154 produces an output on line 156 which indicates the presence of a liquid other than blood in tube 20. When air is in tube 20, neither threshold circuit 150, 154 has an output. The signals on lines 152 and 156 are applied to logic circuit 164 which provides output signals on cable 166 (line 166 A, B, C) indicating the nature of the fluid sensed by sensor 90 and signals on cable 168 (lines 168 A, B, C) indicating the nature of the fluid sensed by sensor 92.

The signals on cables 166 and 168 are applied to controller 170 (FIG. 7). Control input on line 172 is energized when a fluid is to be analyzed. Controller 170 provides outputs on lines 174 to control valves in valve array 26; and pulse generator 176 provides outputs on line 178 to stepping motor 180 which drives peristaltic pump 52. Controller 170 receives pulse inputs on line 182 from clock 184; and when flip-flop 186 is set, gate 188 is conditioned to pass clock pulses to step counter 190. An output from controller 170 on line 192 resets counter 190. The contents of counter 190 are applied over cable 194 to controller 170. In a particular embodiment, controller 170 includes a microprocessor which performs additional analyzer control and data processing functions including the processing of data from analysis modules 44 and 46 over lines 45, 47, and 49 and the display of calculated data results. It will be apparent that a variety of types of controllers may be used with systems in accordance with the invention.

In a particular embodiment controller 170 has a routine of four milliseconds duration and samples signals on each cable 166, 168 at four microsecond intervals. Digital filtering (summing of 128 consecutive sample responses) is used to verify the detection of a gas-liquid interface (e.g., a leading or trailing edge of liquid).

In system operation, pump 52 is initially driven at a sixty-four pulse per second rate. When sensor 22 indicates that a blood sample is to be analyzed, controller 170 causes pulse generator 176 to produce stepping pulses on line 178 at a rate of about 85 per second so that pump 52 propels whole blood at a flow rate to provide a gas-liquid interface (leading or trailing edge) transit time between sensors 90 and 92 in the order of 145–200 milliseconds; and when sensor 22 indicates that a clear liquid such as serum or urine is to be analyzed pulse generator 176 produces stepping pulses on line 178 at a rate of about fifty per second so that pump 52 propels clear liquid at a flow rate to provide a gas-liquid interface (leading or trailing edge) transit time between sensors 90 and 92 in the order of 100–140 milliseconds. In addition to differences in flow velocity depending on the type of liquid, interface velocity is also affected by introduction of air bubbles into a liquid stream, for example to produce a segmented sample.

In response to a start input on line 172, controller 170 applies pulses on line 178 to drive pump 52 at the intermediate rate and commences monitoring fluid sensor 90 for the leading edge of the specified liquid sample, In response to an output from sensor 90 (signals on cable 166) indicative of the leading edge of the desired sample liquid controller 170 sets flip-flop 186 to condition gate 188, and pulses from clock 184 (or other source such as line 178) are passed to step counter 190.

With flip-flop 186 set, controller 170 monitors both sensors 90 and 92, the monitoring of sensor 90 being maintained to confirm the continued presence of the specified liquid and sensor 92 being monitored for the leading edge transition. During this interval, should sensor 90 produce an "air" output (on line 166A), a subroutine is implemented which continues to monitor sensor 90 and when the specified liquid is again sensed (e.g., output on line 166B) controller 170 restarts the timer by an output on line 192 (FIG. 7) which resets counter 190.

If a discontinuity (for example, an air bubble) is sensed by sensor 90 and counter 190 is reset, an interlock circuit may be activated to prevent the leading edge of the liquid sample sensed by sensor 92 from capturing a "short" count.

When sensor 92 produces a liquid sense output (e.g., on line 168B), controller 170 checks that sensors 90 and 92 are sensing the same liquid (e.g., signals on lines 166B and 168B) and repeats the check after a pause. If this comparison check is verified, controller 170 clears flip-flop 186 to capture the count in timer 190 and to set a liquid flag.

The captured count in counter 190 corresponds to the transit time of the leading edge gas-liquid interface between sensors 90 and 92, and this transit time information is used to position that gas-liquid interface at a desired location in valve array 26, e.g., by counting a predetermined multiple of the stored count. Counter 190 is counted down and each zero decrements the predetermined multiple value by one. During this decrement sequence, while pumping of liquid continues, the set flag is checked against the sensor output (e.g., on line 166B) and if a change in fluid is detected, the sample intake sequence is aborted and a new sample intake sequence is begun. In the absence of sample intake abort, pumping continues until the specified multiple of the captured count is reached, which indicates that the leading edge gas-liquid interface is positioned at a desired location in valve array 26 so that 180 $\mu$l sample volume has been drawn into tube 20. A similar control sequence is used to position the trailing edge of the sample to be analyzed.

Further understanding of a sample intake sequence may be had with reference to the diagrams of FIGS. 9–11. In this system, it is desired to position the leading edge of a sample 200 at point 202 in valve array 26 (between valves 30 and 32); and then to position the trailing edge of that sample at point 204 (between valves 34 and 38). With reference to FIG. 9, in response to an analysis start signal on line 172, pump 52 is first driven by motor 180 at the intermediate stepping rate, and controller 170 opens valves 30 and 38 to open the sample flow path between probe 10 and waste receptacle 16. With the tip 12 of probe 10 immersed in the blood to be analyzed in container 14, blood is drawn through probe 10 and line 20 to sensor array 22. Detection of the leading edge transition of blood sample 200 by sensor 90 causes logic 144 to signal that transition on line 166B to controller 170 and stepping of counter 190 commences. When the same leading edge transition is detected by sensor 92, the output on cable 168 switches from line 168A to line 168B, and controller 170 captures that velocity count information in the form of a binary number in counter 190. Pump 52 continues flow of blood sample 200 into valve array 26 with clock pulses being counted and compared with the captured velocity count. While the leading edge desired location 202 may be any distance from sensor array 22, if it is located six centimeters from sensor 92, sample pumping continues for clock pulses equal to five times the captured count. When the count is reached, controller 170 closes valve 30, and open valve 32 to vent the line between valve 30 and pump 52. Pump 52 is then stopped so that about 180 microliters of the blood sample 200 to be analyzed is stored in tube 20 as indicated in FIG. 9.

Probe 10 is then wiped clean and inserted into waste receptacle 16 as indicated in FIG. 10. Controller 170 then closes vent valve 32 and opens probe isolation valve 30 and pump 52 is again driven by stepping motor 180 but at a higher pulse rate (about 85 pulses per second) to draw the blood sample 200 through the valve array 26 and the sample chambers of electrode modules 44 and 46 past the reference junction module 48. At the beginning of flow, vent valve 32 is pulsed seven times, the valve being open for forty milliseconds and closed for about 130 milliseconds in each pulse cycle, so that seven segments 206 of air are inserted into the leading portion of sample 200 as indicated in FIG. 10. This segmenting of sample 200 produces liquid flow transients which clean the surfaces of the flow passage and the analysis chamber of electrode modules 44 and 46. The segmented leading portion of sample 200 is drawn through the analysis chambers and past the reference junction 48 as indicated in FIG. 10.

This introduction of air segments into the leading portion of sample 200 reduces the velocity of the trailing edge of that sample (a transition from liquid to air). When sensor 90 senses the trailing edge transition, logic 144 produces a transition signal on cable 166 (from line 166B to line 166A) to cause controller 170 to again condition gate 188 and pass clock pulses to step counter 190. The sensing of the trailing edge (liquid-air) interface by sensor 92 produces a corresponding signal on cable 168 which causes controller 170 to capture the flow rate count value in counter 190 by closing gate 188. That trailing edge velocity information is used in similar manner to position the trailing edge of sample 200 at location 204. For example where the distance between locations 202 and 204 is about $2\frac{1}{2}$ centimeters, pumping of sample 200 is terminated after clock pulses equal to seven times the captured binary count stored in counter 190. When that number of clock pulses is reached, controller 170 closes electrode isolation valve 38 on the trailing portion of sample 200 as indicated in FIG. 11 so that the sample 200 is held in the analysis chambers of potassium electrode module 44 and sodium electrode module 46. Controller 170 simultaneously opens pinch valve 56 so that electrolyte 208 is drawn from reservoir 58 past reference electrode 210 and reference junction 212 to form a junction between sample and electrolyte as indicated in FIG. 11. About one second after valve 56 has been opened, pump 52 is stopped, the electrodes 44, 46 are allowed to equilibrate with sample 200, and the constituents of that sample are then measured.

When sensor array 22 detects a clear liquid (e.g., serum or urine) to be analyzed (outputs on lines 166C, 168C), pulse generator 176 is controlled to drive motor 180 at a lower pulse rate (about fifty pulses per second) so that excessively large air segments 206 in the liquid sample (due to lower viscosity) are avoided. The trailing edge of that liquid sample is similarly positioned at point 204. Should sensor array 22 detect air during the backflush cycle (using pump 72), depletion of the flush liquid from its storage container is indicated and the operator is alerted to refill that container.

Thus this analyzer control accurately positions minute sample volumes at desired locations within the liquid flow system of the analyzer and provides sensitive response to different liquids processed by the analyzer.

While a particular embodiment of the invention has been shown and described, various modifications will be apparent to those skilled in the art and therefore it is not intended that the invention be limited to the disclosed embodiment or to details thereof, and departures may be made therefrom within the spirit and scope of the invention.

What is claimed is:

1. A system for analyzing a biological fluid comprising an analysis region,
a measurement system connected in sensing relation to said analysis region,
a sample flow path connected between a sample inlet port and said analysis region,
a pump for flowing sample to be analyzed through said sample flow path to said analysis region,
a gas-liquid interface sensor in said flow path, said sensor having a first output when blood is in said flow path, a second output of magnitude different from the magnitude of said first output when serum is in said flow path, and a third output of magnitude intermediate the magnitudes of said first and second outputs when air is in said flow path, and
control means for operating said pump at a first rate and responsive to said interface sensor for positioning the leading edge of a sample of fluid to be analyzed at a predetermined location in said sample flow path and then operating said pump at a second rate different from said first rate determined by the type of fluid detected by said sensor for positioning the sample in said analysis region with the trailing edge of the sample at a second predetermined location in said sample flow path.

2. The system of claim 1 wherein said sensor is arranged to transmit a beam of infrared radiation through said flow path for sensing by a detector on the opposite side of said flow path, and said control means includes threshold logic responsive to changes in the output of said sensor for indicating the nature of the fluid in said flow path.

3. The system of claim 1 and further including logic responsive to said sensor outputs that includes a plurality of threshold detector circuits.

4. The system of claim 1 and further including a second gas-liquid interface sensor in said flow path,
said two gas liquid interface sensor units being spaced a predetermined distance apart along said flow path for sensing the transit time of a gas-liquid interface between said sensor units,
storage means for storing said transit time value as sensed by said interface sensor units, and
said control means is responsive to said stored transit time value for operating said pump for an interval of time that is a predetermined multiple of said stored transit time value for positioning a predetermined volume of liquid to be analyzed in said analysis region.

5. The system of claim 4 wherein each said sensor unit includes a radiation source for directing a beam of infrared radiation through said flow path for sensing by a detector on the opposite side of said flow path.

6. The system of claim 1 wherein said pump is driven by a stepping motor, and further including means responsive to the type of liquid in said flow path as sensed by said sensor for selecting a pump stepping pulse rate.

7. The system of claim 6 and further including a second pump for pumping flush fluid through said sample flow path in a backflush direction and means responsive to said sensor for indicating depletion of flush fluid.

8. The system of claim 1 wherein said measurement system includes an electrochemical electrode with an ion selective membrane that is arranged for exposure to sample in said sample flow path.

* * * * *